(12) United States Patent
Xie et al.

(10) Patent No.: US 7,545,906 B2
(45) Date of Patent: Jun. 9, 2009

(54) METHOD AND SYSTEM FOR BINOCULAR STEROSCOPIC SCANNING RADIOGRAPHIC IMAGING

(75) Inventors: Yali Xie, Beijing (CN); Qitian Miao, Beijing (CN); Yuanjing Li, Beijing (CN); Hua Peng, Beijing (CN); Xueguang Cao, Beijing (CN); Hongsheng Wen, Beijing (CN); Yaohong Liu, Beijing (CN); Quanwei Song, Beijing (CN); Jianping Gu, Beijing (CN); Jin Lin, Beijing (CN); Hongbo Yang, Beijing (CN); Pingan Luo, Beijing (CN)

(73) Assignee: Nuctech Company Limited, Beijing (CN)

( * ) Notice: Subject to any disclaimer, the term of this patent is extended or adjusted under 35 U.S.C. 154(b) by 0 days.

(21) Appl. No.: 11/955,863

(22) Filed: Dec. 13, 2007

(65) Prior Publication Data
US 2008/0205590 A1  Aug. 28, 2008

(30) Foreign Application Priority Data
Dec. 28, 2006  (CN) .......................... 2006 1 0169800
Jul. 20, 2007  (CN) .......................... 2007 1 0130137

(51) Int. Cl.
*G01N 23/00* (2006.01)
(52) U.S. Cl. .......................... 378/25; 378/21
(58) Field of Classification Search .................. 378/41, 378/57, 21–27
See application file for complete search history.

(56) References Cited

U.S. PATENT DOCUMENTS 5,583,904 A * 12/1996 Adams .......................... 378/22

6,081,580 A * 6/2000 Grodzins et al. .............. 378/87

(Continued)

FOREIGN PATENT DOCUMENTS

EP  0 610 084 A2  2/1994

(Continued)

OTHER PUBLICATIONS

"Automated 2-D Cephalometric Analysis on X-Ray Images by a Model Based Approach", by W. Yue et al., *IEEE Transactions on Biomedical Engineering*, 2006, pp. 1-9.

(Continued)

Primary Examiner—Hoon Song
(74) Attorney, Agent, or Firm—Westman, Champlin & Kelly, P.A.

(57) ABSTRACT

In a binocular steroscopic scanning radiographic imaging method, X-rays emitted by the same radiation source are used. The X-rays pass through a double-slit collimator to form two X-ray beam sectors, which are symmetric or asymmetric and have an angle between them. The X-ray beam sectors, after penetrating through an object under detection, are received by the left and right detector array, respectively, then converted into electric signals to be inputted to the respective image acquisition systems, and received by a computer processing system for image processing and displaying. A system corresponding to the method comprises a radiation source, a beam controller, two mutually connected arms of detector arrays, image acquisition systems connected respectively to each of the detector arrays and a computer processing system. The present invention can display the transmission images detected by each of the detector arrays as well as tomograms with different depth reconstructed from the transmission images according to the principle of parallax. The present invention is convenient, fast in detection and realizes with low cost the recognition of objects of different depths.

21 Claims, 6 Drawing Sheets

U.S. PATENT DOCUMENTS 7,283,901 B2 * 10/2007 Luo et al. ............ 701/45
2003/0081720 A1 * 5/2003 Swift et al. ............ 378/41

FOREIGN PATENT DOCUMENTS

GB     2 390 005     12/2003

OTHER PUBLICATIONS

"Image Segmentation for Binocular Stereoscopic Dual-Energy X-Ray Imaging", by Y.S. Yong et al, *Journal of Electronic Imaging*, 2005, pp. 1-9.

European Search Report in corresponding EP Application No. 07119938.4-2319, dated Mar. 10, 2008.

* cited by examiner

METHOD AND SYSTEM FOR BINOCULAR STEROSCOPIC SCANNING RADIOGRAPHIC IMAGING

BACKGROUND OF THE INVENTION

The present application claims priority of Chinese patent applications Serial No. 200610169800.1, filed Dec. 28, 2006 and Serial No. 200710130137.9, filed Jul. 20, 2007, the contents of which are hereby incorporated by reference in their entirety.

1. Field of Invention

The present invention relates to the field of radiographic imaging technology used in a radiographic examination system for large-sized objects, and more particularly to a method and system for binocular steroscopic scanning radiographic imaging, which is used in a radiographic examination system for large-sized containers as well as a security examination system.

2. Description of Prior Art

With the help of the penetrating capability of high-energy X-rays, radiographic imaging technology can look into the inner structure of an object in a non-contact manner so as to obtain a transmission image of the object. For the examination of large objects in the prior art, the operation principle of scanning radiographic imaging is that X-rays are emitted by a radiation source, penetrate through an object to be detected, are received by a detector and then converted into electric signals to be inputted into an image acquisition system, which in turn inputs the image signals into a computer monitor for displaying the detected image. In general, a transmission image by radiographic imaging is actually the projection of every object penetrated by the beam of X-rays and contains no information about transmission depth. Therefore, a scan image will be formed by superimposing the projection of each of the multiple objects along a scanning beam if all the objects are exactly located in the incident direction of X-rays. This is adverse to the examination of an object hidden behind the others. In order to overcome the above problem, in the field of radiographic imaging there has been proposed a relatively mature technology for object reconstruction, which utilizes computerized tomography scanning technique. Unfortunately, this technique has drawbacks of complex structure, high cost, inability to carry out a quick examination on large objects and passing-through ratio.

SUMMARY OF THE INVENTION

In view of the above disadvantages in the prior art, the present invention provides a method and system for binocular steroscopic scanning radiographic imaging, which has a simple structure, low cost and high speed for examination.

To achieve the above object, the present invention provides a method for binocular steroscopic scanning radiographic imaging, which comprises steps of:

1) X-rays emitted by a radiation source through a beam controller to generate two X-ray beams with an angle between them;

2) making said two angled X-ray beams penetrate through objects under detection to generate two transmission images, i.e., left and right transmission images;

3) segmenting said left and right transmission images;

4) matching the results of said segmentation;

5) creating the tomograms of said transmission images in the depth direction and reconstructing the grey levels of the tomograms.

To achieve the above object, the present invention provides a system for binocular steroscopic scanning radiographic imaging, which comprises a radiation source 1, a beam controller 2, a left detector array 4, a right detector array 5, a left image acquisition system 6, a right image acquisition system 7 and a computer processing system 8, and characterized in that:

said radiation source 1 is an X-ray generator for generating two X-ray beams with an angle between them;

said left detector array 4 receives X-rays and converts them into electric signals to be inputted to said left image acquisition system 6;

said right detector array 5 receives X-rays and converts them into electric signals to be inputted to said right image acquisition system 7;

said left image acquisition system 6 receives the electric signals sent by said left detector array 4 and acquires left image data from the electric signals;

said right image acquisition system 7 receives the electric signals sent by said right detector array 5 and acquires right image data from the electric signals;

said computer processing system 8 receives said left and right image data from the left and right image acquisition systems 6 and 7 respectively, segments said left and right image data and matches the result of said segmentation so as to create the tomogram taken along the depth direction of the transmission images and reconstruct the grey level of the tomogram.

With the above configuration, that is, by utilizing the one same radiation source while adding only one set of the detector array and its corresponding image acquisition system, the method and the system of the present invention can offer a transmission image with depth information, which eliminates most of the image superimposition, reflects the true shape and nature of the detected object and lays the foundation for automatic object recognition. Compared with the prior art, the present invention is convenient, fast in detection and realizes with low cost the recognition of objects of different depths. The apparatus of the present invention has a simple structure and low cost; it can be refitted directly in any existing stationary container examination system or applied to any newly-built detection system for large-sized container, either stationary or mobile.

DETAILED DESCRIPTION OF PREFERRED EMBODIMENTS

Hereafter an embodiment of the present invention will be explained in conjunction with the figures.

Figure 1:
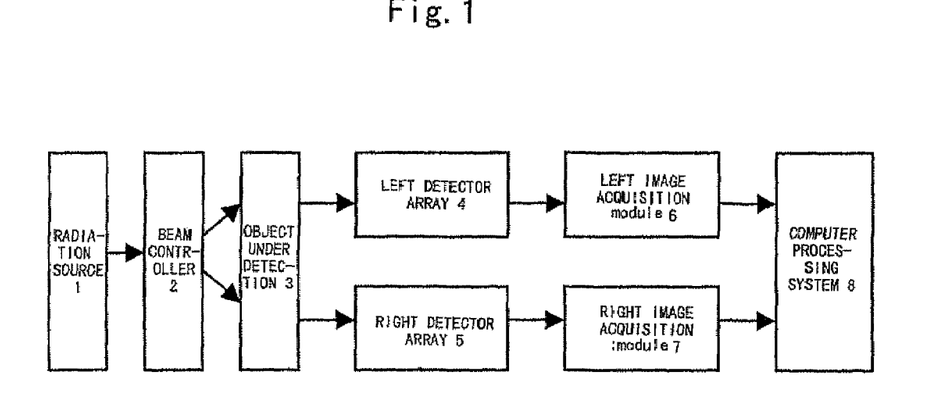
FIG. 1 is an architecture diagram of a binocular steroscopic scanning radiographic imaging system according to the present invention.

FIG. 1 is an architecture diagram of a binocular steroscopic scanning radiographic imaging system according to the present invention, As shown in FIG. 1, the binocular steroscopic scanning radiographic imaging system of the present invention comprises the following devices:

a radiation source 1 being an X-ray generator and able to generate a X-ray beam;

a beam controller for receiving the X-rays emitted by the radiation source 1 and generating two X-ray beams which are symmetric or asymmetric and have an angle between them;

a left detector array 4 for receiving X-rays and converting them into electric signals to be inputted to a left image acquisition system 6;

a right detector array 5 for receiving X-rays and converting them into electric signals to be inputted to a right image acquisition system 7;

the left image acquisition system 6 for receiving the electric signals sent by the left detector array 4 and acquiring left image data from the electric signals;

the right image acquisition system 7 for receiving the electric signals sent by the right detector array 5 and acquiring right image data from the electric signals;

a computer processing system 8 for receiving the left and right image data from the left and right image acquisition systems 6 and 7, processing the left and right image data and displaying each of the detected objection images or the tomograms of different depth constructed from the two images on a computer display.

In the present invention, the radiation source 1, cooperating with the beam controller 2, emits two X-ray beams, which are symmetric or asymmetric and have an angle between them. The X-ray beams, after penetrating through an object under detection 3, are received by the left detector array 4 and the right detector array 5, respectively, and then converted into electric signals to be inputted to the left and right image acquisition systems 6 and 7, respectively. Having been processed by the computer processing system 8, the image data from the left and right image acquisition systems 6 and 7 can be used to display each of the detected objection images or the tomograms of different depth reconstructed from the two images on a computer display.

One preferred embodiment of the present invention uses a double-slit collimator as the beam controller for beam control on the rays emitted by the radiation source.

Figure 2A:
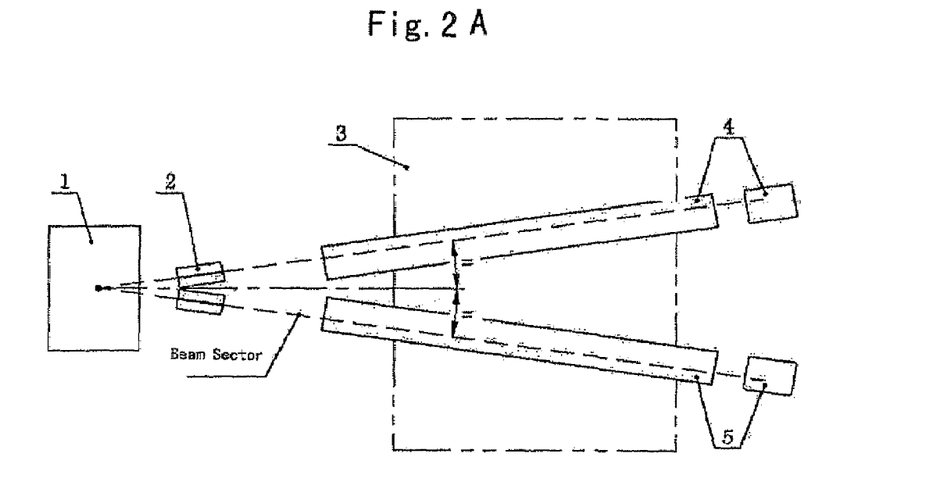
FIGS. 2A and 2B are top views of the schematic layout for the binocular steroscopic scanning radiographic imaging system according to the present invention.
Figure 2B:
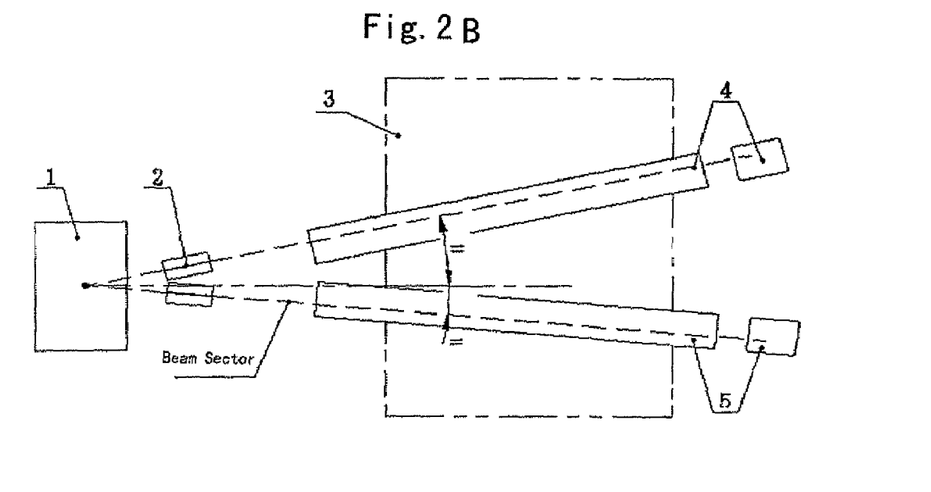
Figure 3:
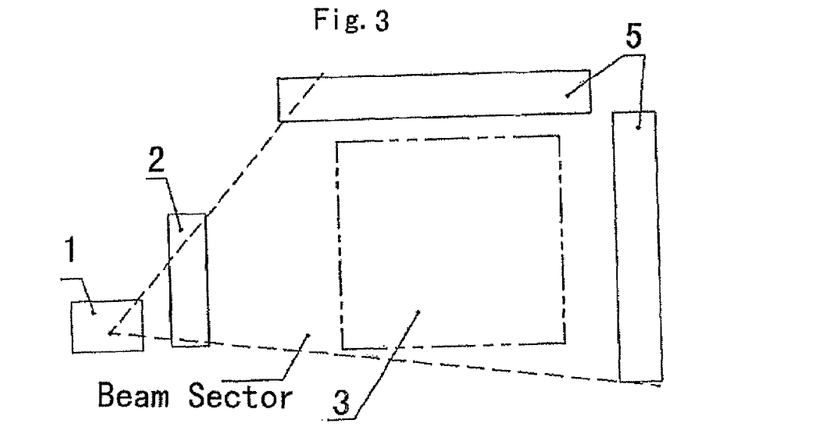
FIG. 3 is a side view of the schematic layout for the binocular steroscopic scanning radiographic imaging system according to the present invention.

FIGS. 2 and 3 are top and side views for schematic layout of the devices needed for implementing the present invention, respectively, where FIG. 2A depicts the case of symmetric ray beams, and FIG. 2B depicts the case of asymmetric ray beams. As shown in FIGS. 2 and 3, two collimation slits are provided in the beam controller to shape the X-rays emitted by the radiation source into two ray beams, either symmetric or asymmetric, with an angle between them. Both of the left detector arrays 4 and 5 face directly the beam sector defined by the collimation slits of the double-slit collimator, scan and examine the object under detection in a symmetric fashion and transmit the electric signals to the corresponding left and right image acquisition systems. Then, the computer processing system 8 carries out image processing to obtain the transmission tomograms containing depth information.

Figure 4:
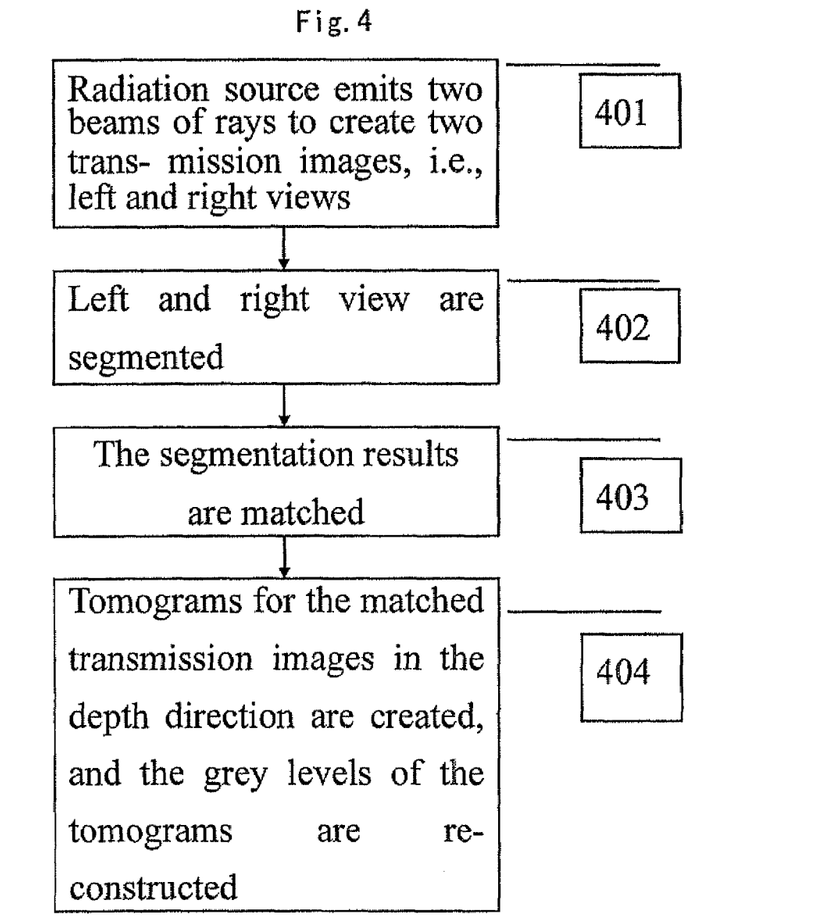
FIG. 4 is a flowchart for the operation of a binocular steroscopic scanning radiographic imaging method according to the present invention.

FIG. 4 is a flowchart for the operation of a binocular steroscopic scanning radiographic imaging method according to the present invention. The specific operation process of the binocular steroscopic scanning radiographic imaging method according to the present invention will be elaborated with reference to FIG. 4.

First, in step 401, one radiation source emits two beams of rays in order to create two transmission images, i.e., left and right ones. In the binocular steroscopic scanning radiographic imaging method, X-rays emitted by the same radiation source are used. The X-rays, after passing through a double-slit collimator, form two beams and penetrate through the object under detection, where the two beams have an angle between them and define a beam sector. The left beam in the beam sector is received by a left detector array and then converted into electric signals to be inputted to a left image acquisition module for generating a left view, while the right beam in the beam sector is received by a right detector array and then converted into electric signals to be inputted to a right image acquisition module for generating a right view. Since the left and right views are formed by passing the X-rays emitted by the single radiation source through the double-slit collimator to generate two beams angled from each other and making the two beams penetrate through the object under detection in a beam sector fashion, respectively, the radiation source for the left and right views is the same and thus consistent in characteristics, and there is certain parallax between the left and right views. The value of the parallax depends on the angle between the two beams as well as the spatial position of the object under detection along the depth direction.

The left and right views are segmented in step 402. Such image segmentation is necessary for the left and right views in order to obtain the tomograms of the transmission views along the depth direction and thus remove the effect of image superimposition. In the present invention, the edge extraction algorithm is applied to image segmentation. The edge extraction method is one of typical discontinuous segmentation methods. In this method, several edges are firstly obtained by detecting local discontinuity and then connected with each other. This edge extraction method is reliable in the segmentation of an X-ray transmission image due to the inherent characteristics of the X-ray transmission image for overlapping objects. In the present invention, Sobel and Canny edge detection operators are used simultaneously to extract edges, which are then synthesized into a resultant edge image. Finally, edge connection is performed on the resultant edge image so as to define enclosed regions. In this way, the segmentation for each of the left and right views can be completed.

Figure 5:
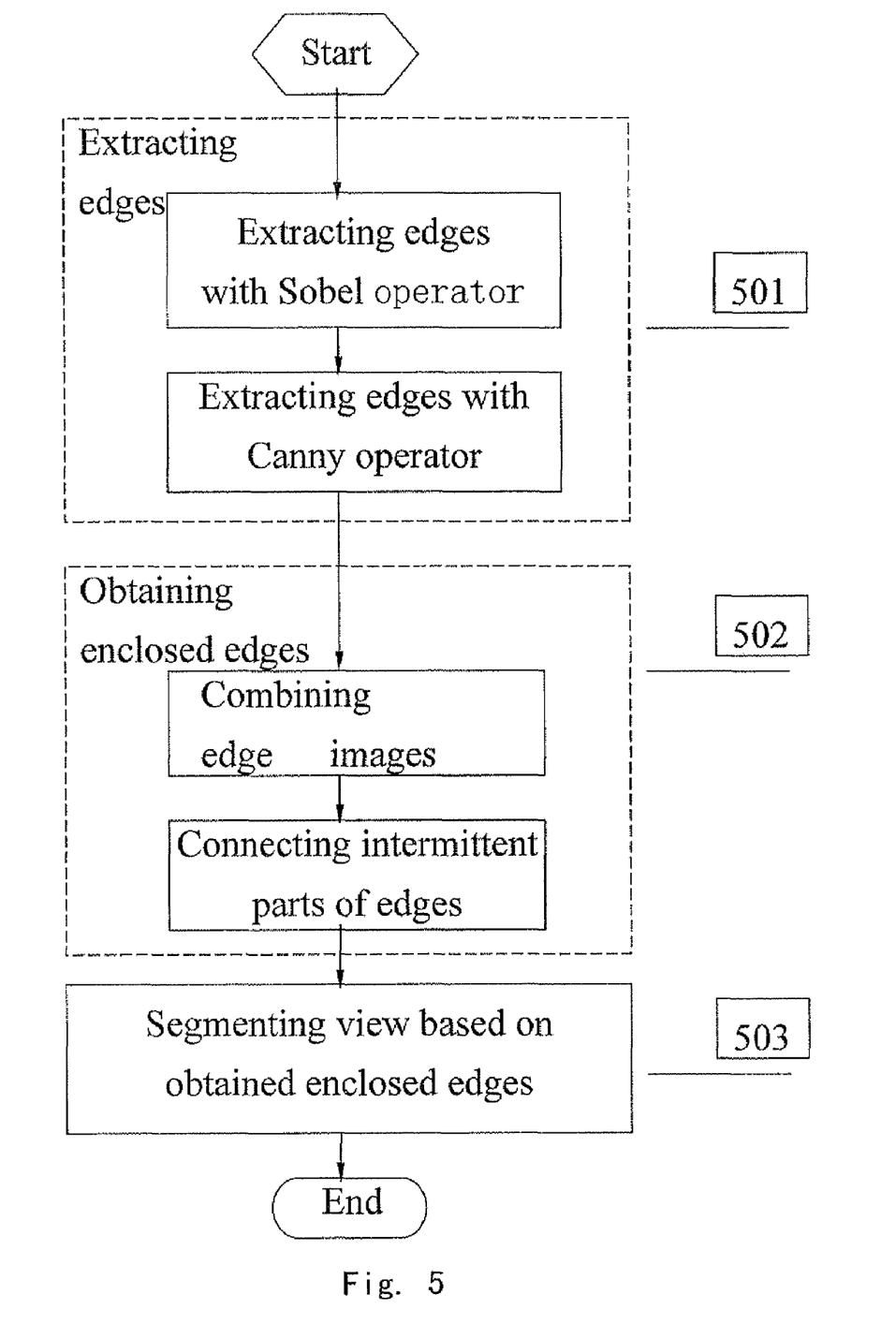
FIG. 5 is a flowchart for image segmentation according to the present invention.

FIG. 5 is a flowchart for image segmentation according to the present invention. The specific operation process of the image segmentation according to the present invention will be elaborated with reference to FIG. 5.

The flow starts with edge extraction in step 501. In the present invention, Sobel and Canny edge detection operators are used simultaneously for edge extraction. For each pixel in an digital image $\{f(i, j)\}$, Sobel edge detection operator calculates a weighted grey level difference between the pixel and its neighbor pixels, i.e., upper, is down, left and right ones, with the nearer neighbor pixel having a larger weight and the farther neighbor pixel having a smaller weight, as defined in the following equation:

$$s(i, j) = |\Delta_x f| + |\Delta_y f|$$
$$= |(f(i-1, j-1) + 2f(i-1, j) +$$
$$f(i-1, j+1)) - (f(i+1, j-1) +$$
$$2f(i+1, j) + f(i+1, j+1))| +$$
$$|(f(i-1, j-1) + 2f(i, j-1) +$$
$$f(i+1, j-1)) - (f(i-1, j+1) +$$
$$2f(i, j+1) + f(i+1, j+1))|$$

The convolution operators are expressed as $$\underbrace{\begin{pmatrix} 1 & 2 & 1 \\ 0 & 0 & 0 \\ -1 & -2 & -1 \end{pmatrix}}_{\Delta_x f}, \underbrace{\begin{pmatrix} 1 & 0 & -1 \\ 2 & 0 & -2 \\ 1 & 0 & -1 \end{pmatrix}}_{\Delta_y f}.$$

Next, a threshold Th is selected, and any pixel (i, j) will be determined as a step-type edge point if it fulfills the in equation S(i, j)>Th, where S(i, j) represents the resultant edge image.

On the other hand, Canny edge detection algorithm generally comprises steps of: smoothing the image with a Gauss filter; calculating the magnitude and direction of gradient by use of finite difference of one-order partial derivative; applying non-maximum suppression image to the magnitude of gradient; and detecting and connecting edges via a double threshold algorithm. Canny operator can reduce pseudo edges by using the double threshold algorithm. Specifically, the non-maximum suppression image is binarized with two thresholds $Th_1$ and $Th_2$, where $2Th_1 \approx Th_2$, to obtain two threshold edge images $N_1(i,j)$ and $N_2(i,j)$. $N_2(i,j)$ is extracted with the higher threshold $Th_2$ and thus has fewer pseudo edges, but there is discontinuity in it. Therefore, it is necessary to connect each intermittent edge into an integral and continuous one in $N_2(i,j)$. The algorithm begins with a pixel referred to as an end point in $N_2(i,j)$, then searches at 8-neighborhood around a pixel in $N_1(i,j)$ corresponding to the end point for a pixel which can be connected with the end point. In this way, the algorithm continuously and repeatedly collects edge points in $N_1(i,j)$ until the intermittent edge in $N_2(i,j)$ is rendered into an uninterrupted outline.

Finally, an enclosed edge image is obtained in step 502. As will be explained later, all of the edges detected by Sobel and Canny edge detection operators should be taken into account to enable edge connection for a satisfactory closed edge image.

In the present invention, the initial edge image results from a logic OR operation between the binary edge images by the above two operators. Each of the edges obtained by the foregoing method usually comprises intermittent parts or even individual edge pixels due to the effect of noise and the like, it is therefore necessary to connect these parts or edge pixels. In the present invention, two edge pixels are connected based on the similarity of them in terms of gradient magnitude and/or gradient direction. For example, a pixel (s, t) can be connected with a pixel (x, y) if the former lies in the neighborhood of the latter, and their gradient magnitudes and gradient directions meet the following requirement with respect to the given thresholds:

$$|\nabla f(x,y) - \nabla f(s,t)| \leq T$$

$$|\nabla \phi(x,y) - \nabla \phi(s,t)| \leq A$$

where $$\nabla f(x, y) = \begin{pmatrix} G_x \\ G_y \end{pmatrix} = \begin{pmatrix} \frac{\partial f}{\partial x} \\ \frac{\partial f}{\partial y} \end{pmatrix},$$

$\phi(x,y)=\arctan(G_x/G_y)$, T represents the threshold for magnitude, and A is the one for angle. As such, by repeating the above determination and connection on all relevant edge pixels, a continuous and closed edge can be acquired.

At step 503, each image of the left and right views is segmented according to a corresponding resultant enclosed edge image. Here, since the image is partitioned into two kinds of regions, i.e., inner and outer, by the closed edge, morphological dilation-erosion operation can be employed to find a pixel belonging to one of the inner regions. Then, starting with this pixel and by use of region growing method, the pixels belonging to the inner region are filled with the value of "1", and the pixels belonging to the outer region are filled with the value of "0". As a result, the binary template for each inner region is obtained, and the image segmentation is then completed.

The above flow starts with searching for edges in the original image with both of Sobel and Canny operators to obtain two edge images. Then, the two edge images are combined into one, and the broken parts or points are connected. The object template is finally extracted by assigning "1" to the regions within the closed edges and "0" to the regions outside.

Now referring to FIG. 4, the segmentation results of the left and right views are matched in step 403. In the present invention, the matching is conducted based on the geometric features of the left and right segmentation results.

First, an object for each of the segmentation results is created, with the set of object properties $\{P_k, k=A,B,\sim,F\}$ comprising:

$P_A$: edge length l;

$P_B$: the coordinate set $\{(x_i,y_i)\}, i=1, 2, \ldots, l$, of edge pixels;

$P_C$: area;

$P_D$: the coordinate of gravity center $$\mu_x = \frac{1}{n}\sum_{i=1}^{n} x_i$$
$$\mu_y = \frac{1}{n}\sum_{i=1}^{n} y_i \quad x_i, y_i \in R_1$$

where R is the set of pixels within an enclosed edge;

$P_E$: perimeter-to-area ratio l/n;

$P_F$: height and width of the object $w=\max(x_i)-\min(x_i)$ $i=1, 2, \ldots, l.$ $h=\max(y_i)-\min(y_i)$ Second, the set of object properties $\{P_k\}$ is allocated with corresponding weights $\{w_k\}$. Assuming that the set of object properties for the left view is $\{P_{i,k}\}$, and the set of object properties for the left (right) view is $\{P_{j,k}\}$, where i and j serve as object indexes in the left and right views, respectively, the following equation can be calculated:

$$E_{i,j} = \sum_{k=1}^{t} w_k |P_{i,k} - P_{j,k}|$$

Then, a threshold $Th_{mat}$ is selected in such a manner that, when $E_{i,j}$ reaches its minimum and $E_{i,j} < TH_{mat}$ holds, the corresponding i and j designate the matched objects in the left and right views, that is, i and j are the indexes for the segmentation results.

For example, the matching result in the above example is (a) being matched with (b), (c) with (d) and (e) with (f). For a successfully matched object, its absolute parallax is calculated by subtracting its position in one of the left and right views from that in the other view:

$$pr_k = \mu_{L,x,k} - \mu_{R,x,k}$$

$\mu_{L,x,k}$ denotes the horizontal coordinate of the gravity center for the kth matched object in the left view, and $\mu_{R,x,k}$ denotes the horizontal coordinate of the gravity center for the kth matched object in the right view.

In step 404, the tomograms of the transmission image are constructed in the depth direction, and the grey level of each tomogram is reconstructed. To be more specific, based on the matched result of the left and right view as well as the corresponding absolute parallax, the shape tomograms of the transmission image can be reconstructed in the depth direction, and the grey level for each tomogram can also be reconstructed. In this way, the objects overlaying on each other are classified into different tomograms, thereby eliminating the effect of superimposition in the transmission image.

Figure 8:
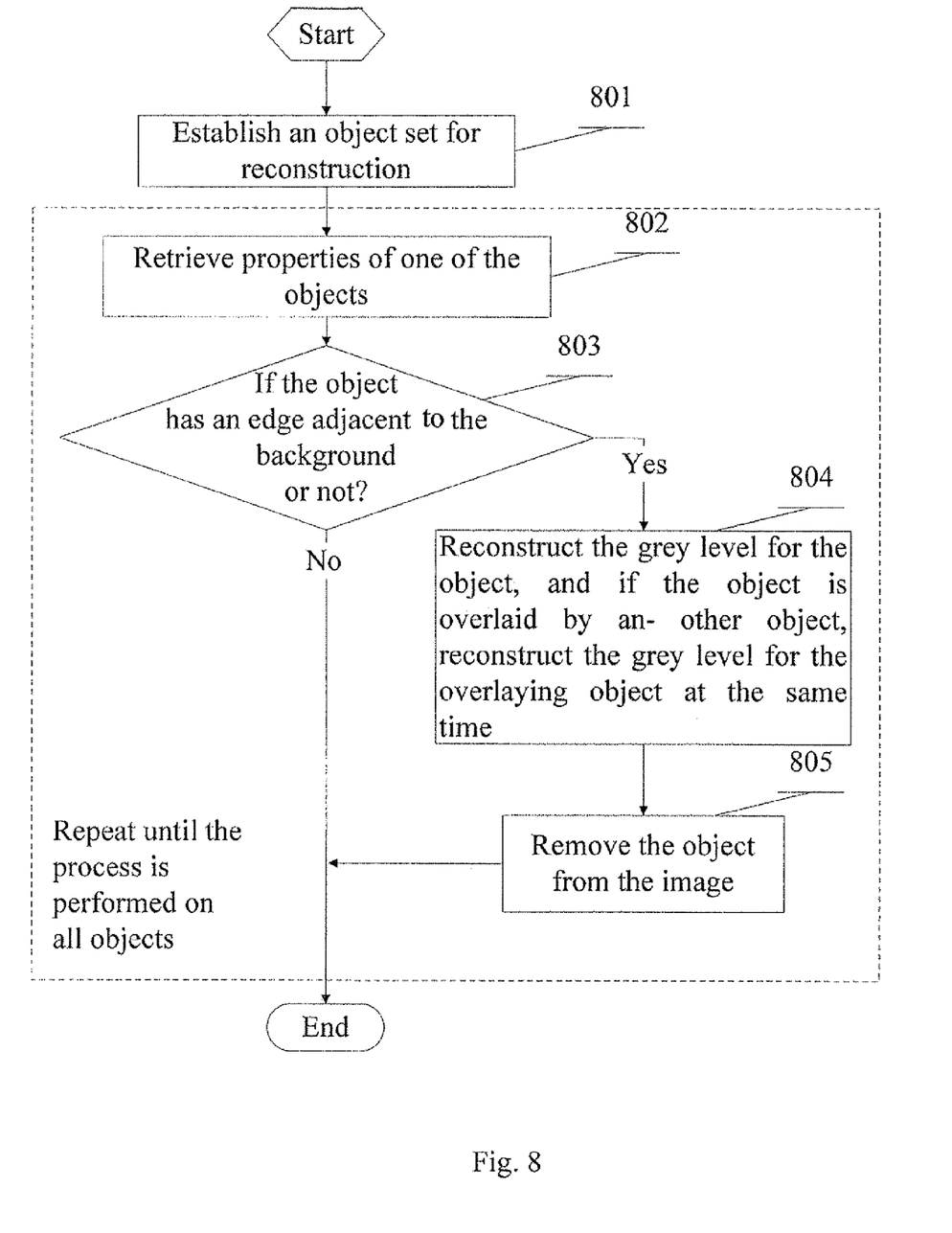
FIG. 8 is a flowchart for grey level reconstruction according to the present invention.

FIG. 8 shows a detailed flowchart for grey level reconstruction according to the present invention. The concrete implementation process according to the present invention will be elaborated with reference to FIG. 8.

In the present invention, the grey level for each object is reconstructed by peeling off the grey level layer by layer from the outermost to the innermost. In particularly, the grey level for the matched object on the outermost lay (directly adjacent to the background region) is first reconstructed and peeled off from the image. Then, the object on the next outermost lay is processed in the same way. This procedure is repeated until the grey level reconstruction has been performed on all the matched objects. The specific steps are:

step 801: establishing a candidate object set for grey level reconstruction by using the objects obtained in the step 404;

step 802: retrieving the properties of one of the objects;

step 803: determining whether the retrieved object has an edge adjacent to the background region;

step 804: reconstructing the grey level for the object if the retrieved object has an edge adjacent to the background region, and, if the object is overlaid by another object, reconstructing the grey level for the overlaying object;

step 805: removing the object from the image.

For each object in the object set, the steps 802 to 805 are repeated until the grey level reconstruction has been performed on all the matched objects.

During the process of grey level reconstruction, each of the objects comprises only two types of parts, one being the part adjacent to the background region, the other being the part overlaid by another object. Notice, for an object which is initially overlaid completely and thus has no edge adjacent to the background, some of the region where the overlaying object lies must turn into part of the background region and thus can be treated as a new background region after a sufficient number of peeling off, and therefore the overlaid object will has an edge adjacent to the new background region. The reconstructed grey level for the object equals to the difference between the grey level outside the edge and that inside the edge, that is, $$S_{obj} = (S_{out} - S_{in}).$$

Having been reconstructed, the object is removing from the original image. Specifically speaking, the grey level for the object region adjacent to the background is added to $S_{obj}$ to become the background grey level $S_{out}$, while the grey level for the region overlaid by another object is added to $S_{obj}$ and then multiplied with a nonlinear correcting coefficient $\alpha_{rst}$, that is, $$S_{rst} = \alpha_{rst}(S_{org} + S_{obj}).$$

Figure 6:
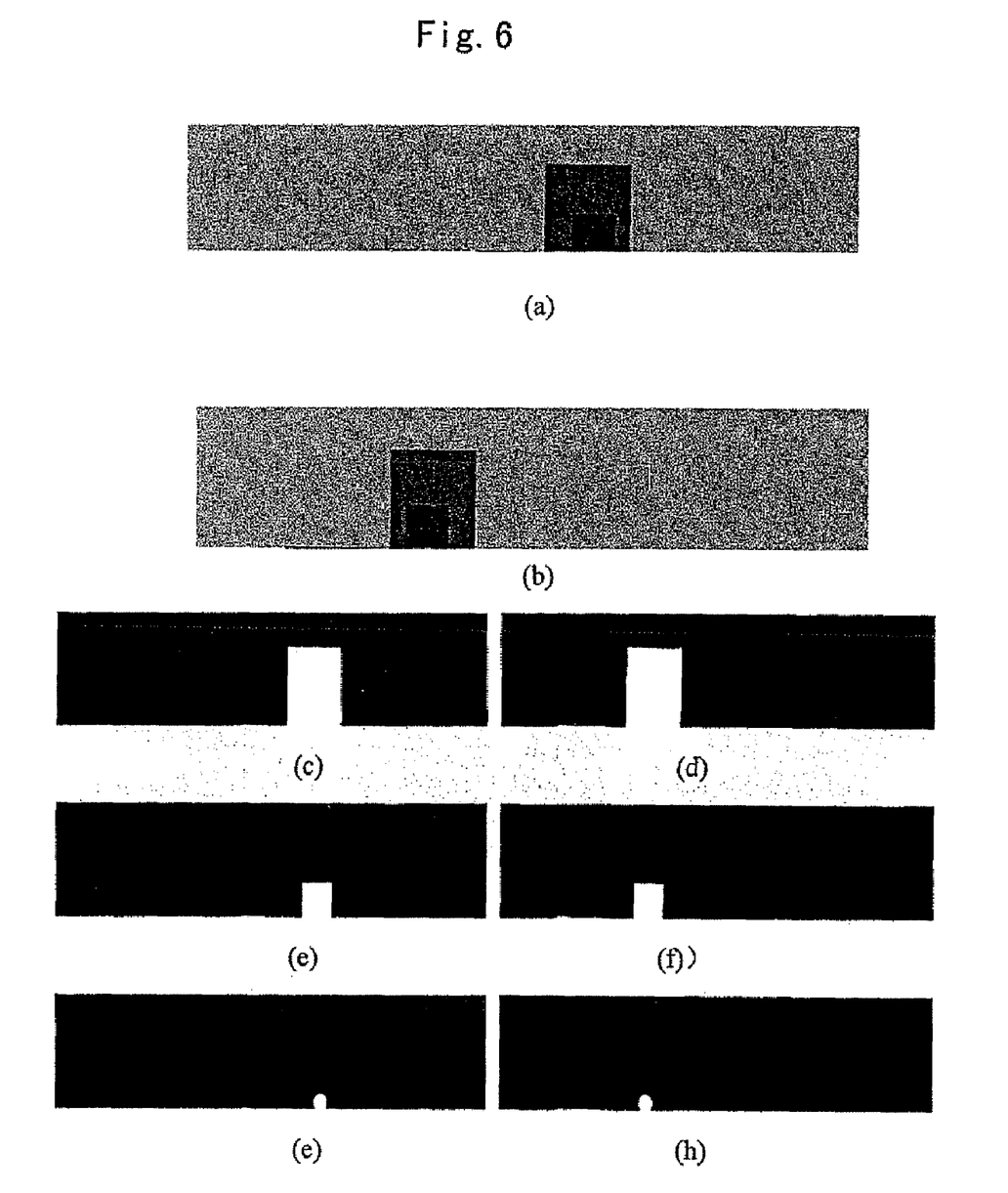
FIG. 6 is a diagram showing the effect after segmenting left and right views of three-layer superimposition according to the present invention.

FIG. 6 is a diagram showing the effect after segmenting left and right views of three-layer superimposition according to the present invention. As shown in FIG. 6, (a) represents the left view, while (b) represents the right view. The effect after segmenting the left and right views is: (c) for the template of the first object in the left view and (d) for the template of the first object in the right view, with the pair of object templates being two larger rectangles as shown in the figure; (e) for the template of the second object in the left view and (f) for the template of the second object in the right view, with the pair of object templates being two smaller rectangles as shown in the figure; and (g) for the template of the third object in the left view and (h) for the template of the third object in the right view, with the pair of object templates being two ellipses as shown in the figure.

Figure 7:
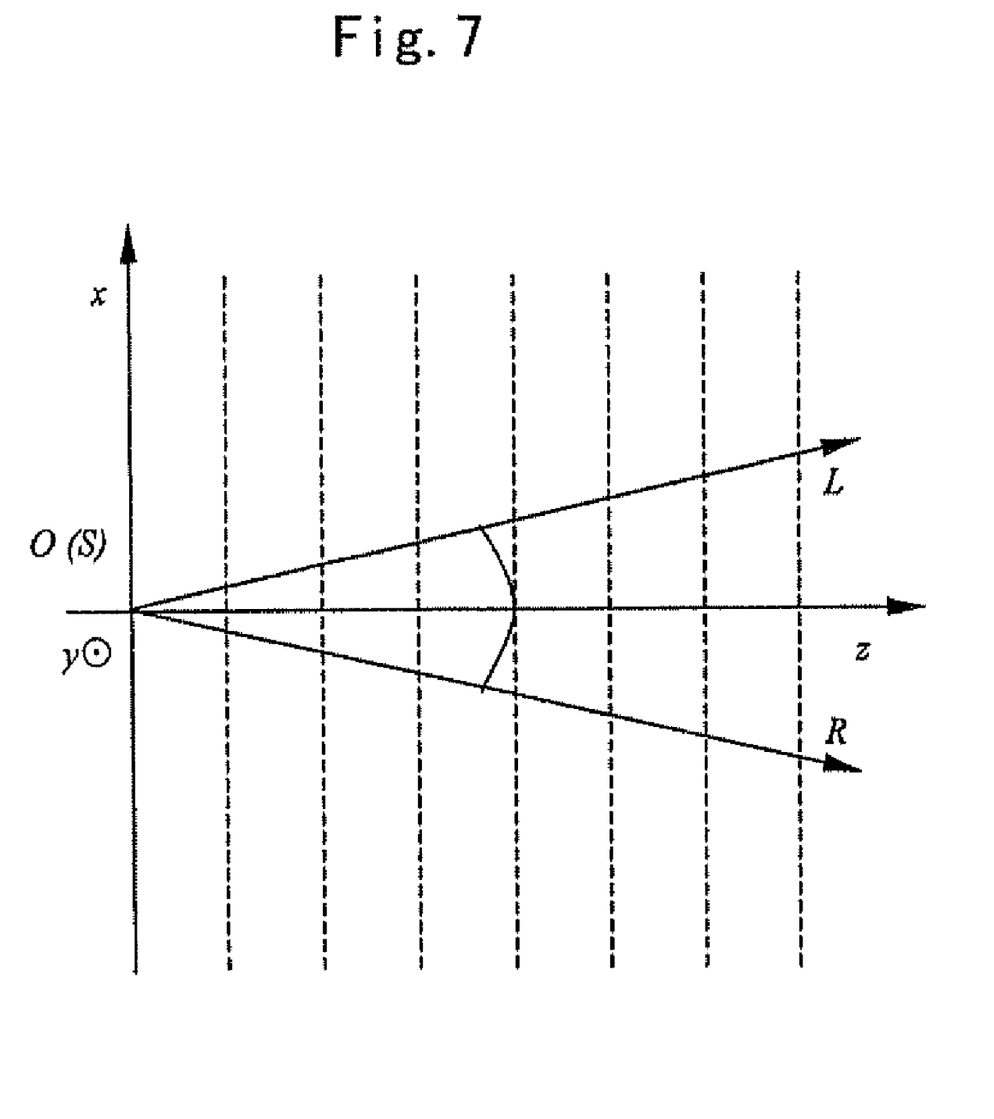
FIG. 7 is a schematic diagram for binocular steroscopic tomograms of the transmission image in the depth direction according to the present invention.

FIG. 7 is a schematic diagram for binocular steroscopic tomograms of the transmission image in the depth direction according to the present invention. As shown in FIG. 7, a spatially orthogonal coordinates is established such that the scanning direction (vertically upward) is denoted by the positive direction of x axis, the alignment direction of the detector array (outward vertically to the plane of the figure) is denoted by the positive direction of y axis, the horizontally rightward direction is denoted by the positive direction of z axis, and the location O of the radiation source S is taken as the origin of the coordinates. The tomograms are a series of spatial planes parallel to the x-O-y plane, and what is shown by the broken line in the figure denotes the projection of the tomogram planes in the x-O-z plane. In FIG. 7, L represents the projection of left primary beam in the x-O-z plane, while R represents the projection of right primary beam in the x-O-z plane. $\theta$ is the angle between the projection of the left and right ray beam in the x-O-z plane.

The tomogram depth means the distance between the tomogram plane and the x-O-y plane, and relationship between the tomogram depth and the parallax pr is $$\tan(\theta/2) = pr/z.$$

Each of the matched objects is depicted in the tomogram with the corresponding depth which is calculated as $$z = pr/\tan^{-1}(\eta/2) = (\mu_{x,i} - \mu_{x,j})/\tan^{-1}(\theta/2)$$

where $\mu_{x,i}$ and $\mu_{x,j}$ are the horizontal coordinates of the gravity centers in the left and right views, respectively, for the matched objects.

In the above equation, the parallax is directly proportional to the tomogram depth. This can be proven as shown in FIG. 7, in which the object denoted by (a) and (b) lies on the first layer and thus has a minimum depth since its parallax is the smallest; the object denoted by (c) and (d) lies on the second layer and thus has a medium depth since its parallax is in the middle; and the object denoted by (e) and (f) lies on the third layer and thus has a maximum depth since its parallax is the greatest.

The foregoing description gives only the preferred embodiments of the present invention and isn't intended to limit the present invention in any way. Thus, the various modifications and variations made by those skilled in the art without departing from the principle of the present invention should be encompassed by the scope of the present invention defined by the appended claims.

What is claimed is:

1. A binocular steroscopic scanning radiographic imaging method, which comprises steps of:
    generating two X-ray beams with an angle between them from X-rays emitted by a radiation source;
    making said two angled X-ray beams penetrate through objects under detection to obtain data for left and right transmission images;
    segmenting said left and right transmission images;
    matching the results of said segmentation; and
    creating tomograms for the matched transmission image in the depth direction and reconstructing the grey levels of the tomograms.

2. The binocular steroscopic scanning radiographic imaging method of claim 1, wherein the X-rays forms the X-ray beams with an angle between them by passing through a beam controller, and the X-rays penetrates through the objects under detection in the shape of beam sector.

3. The binocular steroscopic scanning radiographic imaging method of claim 1, wherein the segmentation of said left and right transmission images is implemented according to an edge extraction algorithm.

4. The binocular steroscopic scanning radiographic imaging method of claim 3, wherein the segmentation of said left and right transmission images further comprises steps of:
    extracting edges in each of the said left and fight transmission images;
    obtaining enclosed edges in these images; and
    segmenting these images according to the obtained enclosed edges.

5. The binocular steroscopic scanning radiographic imaging method of claim 1, wherein the matching of the results of said segmentation is implemented according to the geometric characteristics of the left and right segmentation results.

6. The binocular steroscopic scanning radiographic imaging method of claim 1, wherein the matching of the results of said segmentation further comprises steps of:
    creating objects for the segmentation results;
    allocating corresponding weights to the property set of the objects.

7. The binocular steroscopic scanning radiographic imaging method of claim 1, wherein the creation of tomograms for the matched transmission images in the depth direction is implemented based on the matched results of the left and right images as well as the corresponding absolute parallax.

8. The binocular steroscopic scanning radiographic imaging method of claim 1, wherein the reconstruction of grey level for the tomograms is implemented by peeling off grey level layer by layer from the outermost to the innermost, in particular, the grey level for the matched object on the outermost lay adjacent to the background is first reconstructed and peeled off from the image, in sequence, the object on the next outermost lay is then processed in the same way, and this procedure is repeated until the grey level reconstruction has been performed on all of the matched objects.

9. The binocular steroscopic scanning radiographic imaging method of claim 6, wherein the reconstruction of grey level for the tomograms further comprises steps of:
    establishing a candidate object set for grey level reconstruction by using said objects;
    retrieving the properties of one of said objects;
    determining whether the retrieved object has an edge adjacent to the background;
    reconstructing the grey level for the object if the retrieved object has an edge adjacent to the background, and, if the object is overlaid by another object, reconstructing the grey level for the overlaying object; and
    removing the object from the image;
    and for each object in the object set, the steps 2) to 5) are repeated until the grey level reconstruction has been performed on all of the matched objects.

10. The binocular steroscopic scanning radiographic imaging method of claim 5, wherein said edge extraction in the image is conducted by using Sobel and Canny edge detection operator simultaneously.

11. The binocular steroscopic scanning radiographic imaging method of claim 10, wherein, for each pixel in an digital image $\{f(i,j)\}$, said Sobel edge detection operator calculates a weighted grey level difference between the pixel and its neighbor pixels, i.e., upper, down, left and right ones, with the nearer neighbor pixel having a larger weight and the farther neighbor pixel having a smaller weight.

12. The binocular steroscopic scanning radiographic imaging method of claim 10, wherein the edge extraction by using said Canny edge detection operator comprises steps of:
    smoothing an image with a Gauss filter;
    calculating the magnitude and direction of gradient by use of finite difference of one-order partial derivative;
    applying non-maximum suppression to the magnitude of gradient; and
    detecting and connecting edges via a double threshold algorithm.

13. The binocular steroscopic scanning radiographic imaging method of claim 4, wherein
    the obtaining of enclosed edges in these images is conducted such that two edge pixels are connected based on the similarity between them in terms of gradient magnitude or gradient direction.

14. The binocular steroscopic scanning radiographic imaging method of claim 4, wherein
    the image segmentation according to the obtained enclosed edges comprise steps of:
    finding a pixel belonging to a region inside one of the enclosed edges by using morphological dilation-erosion operation;
    starting with this pixel and by use of region growing method, filling the pixels belonging to the region inside the enclosed edge with the value of "1", while filling the pixels belonging to the region outside the enclosed edge with the value of "0", and thus obtaining binary templates for all the regions inside the enclosed edges to complete the image segmentation.

15. The binocular steroscopic scanning radiographic imaging method of claim 9, wherein the grey level is reconstructed for the object retrieved if the object has an edge adjacent to the background, and, if the object is overlaid by another object, the grey level is reconstructed at the same time for the overlaying object; then, the object is removed from the object set and the image.

16. A binocular steroscopic scanning radiographic imaging system comprising a radiation source, a left detector array, a right detector array, a left image acquisition system, a right image acquisition system and a computer processing system, wherein said radiation source is an X-ray generator for generating two X-ray beams with an angle between them;

said left detector array receives X-rays and converts them into electric signals to be inputted to said left image acquisition system;

said right detector array receives X-rays and converts them into electric signals to be inputted to said right image acquisition system;

said left image acquisition system receives the electric signals sent by said left detector array and acquires left image data from the electric signals;

said right image acquisition system receives the electric signals sent by said right detector array and acquires right image data from the electric signals;

said computer processing system receives said left and right image data from the left and right image acquisition systems respectively, segments said left and right image data and matches the results of said segmentation so as to create tomograms of the matched transmission images in the depth direction, reconstructs grey levels of the tomograms and display the transmission tomograms with different depth reconstructed from both of the left and right image data.

17. The binocular steroscopic scanning radiographic imaging system of claim 16, further comprising a beam controller for receiving the X-rays emitted by the radiation source and generating two X-ray beams which are symmetric or asymmetric and have an angle between them.

18. The binocular steroscopic scanning radiographic imaging system of claim 17, wherein said beam controller is a double-slit collimator.

19. The binocular steroscopic scanning radiographic imaging system of claim 18, wherein two collimation slits are provided in said double-slit collimator to shape the X-rays emitted by said radiation source into two beam sector, either symmetric or asymmetric, with an angle between them.

20. The binocular steroscopic scanning radiographic imaging system of claim 16, wherein said detector arrays is arranged in 'L'-type arms.

21. The binocular steroscopic scanning radiographic imaging system of claim 16, wherein said computer processing system can also display the images of the objects under detection, based on the left and right image data, respectively.

* * * * *

UNITED STATES PATENT AND TRADEMARK OFFICE
CERTIFICATE OF CORRECTION

PATENT NO. : 7,545,906 B2 Page 1 of 1
APPLICATION NO. : 11/955863
DATED : June 9, 2009
INVENTOR(S) : Yali Xie et al.

It is certified that error appears in the above-identified patent and that said Letters Patent is hereby corrected as shown below:

Col. 8, line 56, change "$z = pr/tan^{-1}(\eta/2) = (\mu_{x,j} - \mu_{x,j})/tan^{-1}(\theta/2)$" to -- $z = pr/\tan^{-1}(\theta/2) = (\mu_{x,i} - \mu_{x,j})/\tan^{-1}(\theta/2)$ --.

Claim 4, line 37, change "fight" to --right--.

Signed and Sealed this

Thirtieth Day of November, 2010

David J. Kappos
*Director of the United States Patent and Trademark Office*

UNITED STATES PATENT AND TRADEMARK OFFICE
CERTIFICATE OF CORRECTION

PATENT NO.       : 7,545,906 B2           Page 1 of 1
APPLICATION NO.  : 11/955863
DATED            : June 9, 2009
INVENTOR(S)      : Yali Xie et al.

It is certified that error appears in the above-identified patent and that said Letters Patent is hereby corrected as shown below:

Col. 8, line 56, change "$z = pr/tan^{-1}(\eta/2) = (\mu_{x,j} - \mu_{x,j})/tan^{-1}(\theta/2)$" to -- $z = pr/\tan^{-1}(\theta/2) = (\mu_{x,i} - \mu_{x,j})/\tan^{-1}(\theta/2)$ --.

Claim 4, Column 9, line 37, change "fight" to --right--.

This certificate supersedes the Certificate of Correction issued November 30, 2010.

Signed and Sealed this
Twenty-fifth Day of January, 2011

David J. Kappos
*Director of the United States Patent and Trademark Office*